United States Patent [19]
Britcher et al.

[11] Patent Number: 4,870,079
[45] Date of Patent: Sep. 26, 1989

[54] DERIVATIVES OF 5-METHYL-10,11-DIHYDRO-5H-DIBENZO[A,D]CYCLOHEPTEN-5,10-IMINE

[75] Inventors: Susan F. Britcher, Norristown; Wayne J. Thompson, Green Lane; Terry A. Lyle, Lederach; Sandor L. Varga, Harleysville, all of Pa.

[73] Assignee: Merck & Co., Inc., Rahway, N.J.

[21] Appl. No.: 175,469

[22] Filed: Mar. 30, 1988

Related U.S. Application Data

[63] Continuation of Ser. No. 87,125, Aug. 19, 1987, abandoned, which is a continuation-in-part of Ser. No. 36,392, Apr. 9, 1987, abandoned, which is a continuation-in-part of Ser. No. 904,940, Sep. 8, 1986, abandoned.

[51] Int. Cl.$^4$ .................... A61K 31/46; C07D 471/08
[52] U.S. Cl. ........................................ 514/289; 546/72
[58] Field of Search ................. 546/72; 514/289; 540/556

[56] References Cited

U.S. PATENT DOCUMENTS 3,892,756  7/1975  Nedelec et al. ................. 546/72
4,399,141  8/1983  Anderson et al. ............... 514/294

FOREIGN PATENT DOCUMENTS 0264183  9/1987  European Pat. Off. .

OTHER PUBLICATIONS

Dagani, "New Anticonv. Agents Have Unusual Struct.", Chem. & Eng. News, Sep. 29 (1986).
Meldrum, "Poss. Ther. Appl. of Antag. of Excitatory Amino Acid Neurotrans.", Clin. Sci., 68, pp. 113–122 (1985).
Rothman, "Excitotoxicity & NMDA Receptor", TINS, vol. 10, No. 7 (1987).
Klockgetner et al., Chem. Abstracts, vol. 106 (1987), entry 169537y.

Primary Examiner—Mukund J. Shah
Assistant Examiner—Andrew G. Rozycki
Attorney, Agent, or Firm—William H. Nicholson; Joseph F. DiPrima

[57] ABSTRACT

Fluoro-and hydroxy-derivatives of 5-methyl-10,11-dihydro-5H-dibenzo[a,d]cyclohepten-5,10-imines wherein the substituents are on non-benzenoid carbons are active anticonvulsants and antagonists of N-methyl-D-aspartate.

10 Claims, No Drawings

DERIVATIVES OF 5-METHYL-10,11-DIHYDRO-5H-DIBENZO[A,D-]CYCLOHEPTEN-5,10-IMINE

This is a continuation of application Ser. No. 087,125, filed Aug. 19, 1987, now abandoned, which is a continuation-in-part of copending application Ser. No. 036,392, filed Apr. 9, 1987 now abandoned, which in turn is a continuation-in-part of application, Ser. No. 904,940, filed Sept. 8, 1986, now abandoned.

SUMMARY OF THE INVENTION

This invention is concerned with a compound of structural formula I

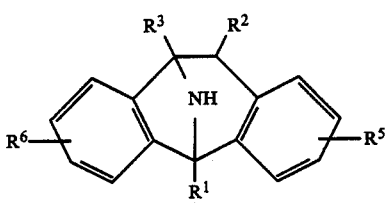

wherein $R^1$, $R^2$, $R^3$, $R^5$ and $R^6$ are as defined hereinafter. The compounds represented thereby are useful as anticonvulsant agents and N-methyl-D-aspartate (NMDA) antagonists useful in the treatment of neurodegenerative diseases.

The invention is also concerned with pharmaceutical compositions comprising one or more of the novel compounds represented by structural formula I and methods of treatment of convulsions and neurodegenerative diseases by administration of the novel compounds or pharmaceutical formulation thereof.

The invention is also concerned with novel processes for preparing the novel compounds.

BACKGROUND OF THE INVENTION

5-Methyl-10,11-dihydro-5H-dibenzo[a,d]cyclohepten-5,10-imine (MK-801) and many derivatives thereof are the subject of U.S. Pat. No. 4,399,141 of Anderson et al., the disclosure of which is incorporated herein by reference. The principle clinical utility of MK-801 has been shown to be anticonvulsant. It also has been reported to be an NMDA antagonist useful in the treatment of neurodegenerative diseases such as Alzheimer's disease.

Now with the present invention there are provided new hydroxy- and fluoro-derivatives of MK-801 in which the substituents are on non-benzenoid carbons, one of the derivatives being a major mammalian metabolite of MK-801. These new derivatives are also anticonvulsants and NMDA antagonists useful in the prevention and/or treatment of neurodegeneration in pathological conditions such as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-pontocerebellar atrophy, anoxia such as from drowning, spinal cord injury and poisoning by exogenous NMDA poisons (e.g. some forms of lathyrism).

DETAILED DESCRIPTION OF THE INVENTION

The novel compounds of this invention are represented by structural formula I

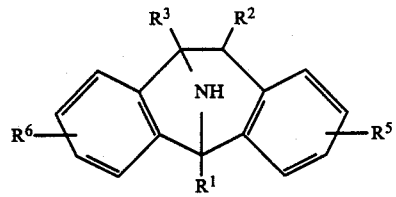

or a pharmaceutically acceptable salt thereof, wherein
  $R^2$ and $R^3$ are independently:
    (1) hydrogen,
    (2) hydroxy, or
    (3) fluoro; and
  $R^1$ is
    (1) —CH$_2$F,
    (2) —(CH$_2$)$_2$F
    (3) —CH$_2$OH,
    (4) —CH$_3$,
    (5) —CH$_2$COOR$^4$, wherein $R^4$ is C$_{1-3}$alkyl,
    (6) —CH(OH)COOR$^4$,
    (7) —CH(OH)CH$_2$OH,
    (8) —CH$_2$CH$_2$OH, or
    (9) —CH$_2$CH$_3$;
  $R^5$ and $R^6$ are independently
    (1) hydrogen,
    (2) halogen,
    (3) C$_{1-5}$alkoxy,
    (4) trifluoromethylthio,
    (5) cyano,
    (6) carboxy, or
    (7) hydroxy,
with the proviso that if both $R^2$ and $R^3$ are hydrogen, then $R^1$ is not —CH$_3$, —CH$_2$CH$_3$, —CH$_2$CH$_2$OH or —CH$_2$COOR$^4$.

A preferred compound is that wherein $R^2$ is hydroxy, in which case if the —OH is exo- it is a major mammalian metabolite of MK-801.

In the novel compounds wherein $R^2$ is other than hydrogen, the $R^2$ substituent is in either the exo- or endo-conformation and both of these isomers are contemplated as part of this invention.

The novel compounds also can be resolved into their optical isomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary. The enantiomers and mixtures thereof are also within the scope of the present invention.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like.

In the anticonvulsant method of treatment aspect of the present invention, the novel imines of this invention are useful as anticonvulsants at a dosage level of from about 0.01 to about 20 mg per kilogram of body weight preferably about 0.05-2 mg/kg of body weight on a regimen of 1-4 times a day.

In the novel method of treatment of neurodegeneration a dosage level of about 0.01 to 50 mg/kg, preferably about 0.05 to 10 mg/kg and especially about 0.05 to 0.5 mg/kg/day and may be administered on a regimen of 1 to 4 times per day.

It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a member of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The novel processes of this invention for preparing the 10-hydroxy compound is illustrated as follows:

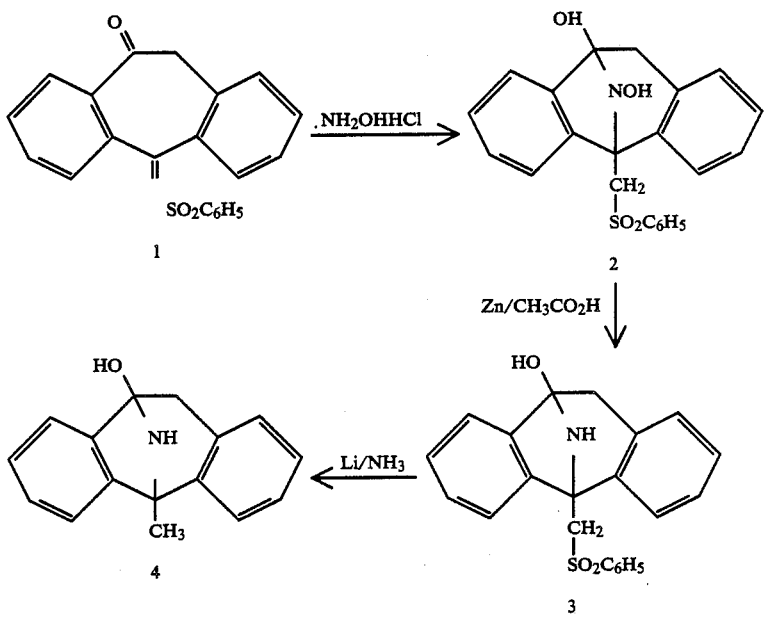

Hydroxylamine is added across the seven-membered ring of 1 by mixing 1 and the hydroxylamine hydrochloride in the presence of sodium acetate in an ethereal solvent such as ether, THF, 1,2-dimethoxyethane or the like at about 10° to 25° C. for about 10 to 24 hours. The product isolated therefrom is treated with nascent hydrogen to hydrogenolyze the —OH group. The hydrogen is conveniently generated by the action of an acid on a metal, such as zinc and acetic acid, zinc and HCl, sodium and ethanol or the like to provide 3. The arylsulfonyl group is then removed from 3 by treatment with liquid $NH_3$/lithium at about −95° to −65° C., preferably about −78° C. in the presence of a lower alkanol such as butanol followed by refluxing for about 3 to 6 hours.

The 11-endo-hydroxy derivative is prepared as shown below:

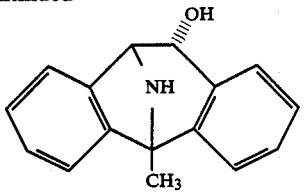

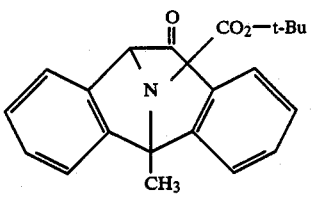

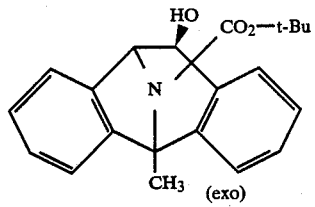

The aziridino compound, 5, is treated with a mixture of sodium acetate or potassium acetate and acetic acid at about 60° C. to reflux temperature for about 15 minutes to 2 hours followed by neutralization and isolation by extraction techniques.

The product, 6, is treated with potassium hydroxide in methanol under anhydrous conditions at about 15° to 30° C. for about 2 to 5 hours. Concentration to dryness and extraction with water affords the aqueous insoluble product 7.

Alternatively, the 11-endo-hydroxy compound is obtained along with the 11-exo isomer as follows:

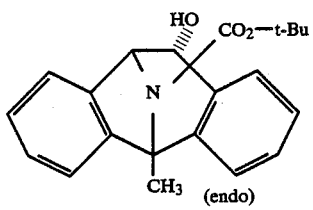

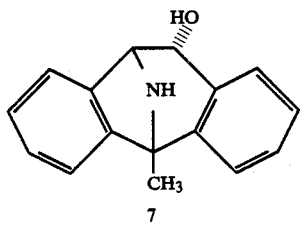

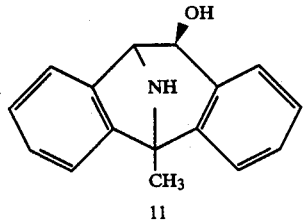

In this novel process, the oxo compound, 8, is reduced by treatment with diisobutylaluminum hydride (Dibal-H) in an ethereal solvent such as ether, THF, dimethoxyethane or the like at about −90° to −60° C., preferably about −78° C. for about 1 to 3 hours. After quenching excess Dibal-H with an alcohol, the product, 9 and 10 (2:1), is isolated by extraction techniques.

The mixture of 9 and 10 is deprotected by treatment with ethanolic HCl at about −10° to +10° C., for about 5 to 16 hours followed by preparative chromatography to separate the epimers.

The 11-exo-hydroxy compound also may be prepared in accordance with the following reaction scheme:

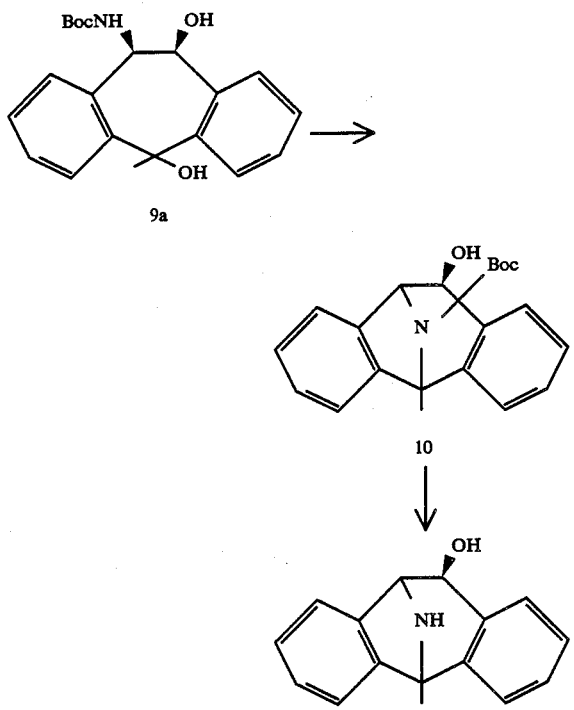

The ring closure to compound 10 is effected by treatment of compound 9a with p-toluenesulfonic acid in an inert solvent, such as benzene or toluene at about 35° to 70° C. for about 3 to 8 hours. The t-butoxycarbonyl group is then removed with trifluoroacetic acid by standard procedures.

The 10-fluoro derivative of MK-801 is prepared by treating the corresponding 10-hydroxy compound (4) with diethylaminosulfurtrifluoride (DAST) in an inert organic solvent such as a chlorinated hydrocarbon such as chloroform or methylene dichloride at about 15° to 30° C. for about 30 minutes to 2 hours. The reaction is illustrated as follows:

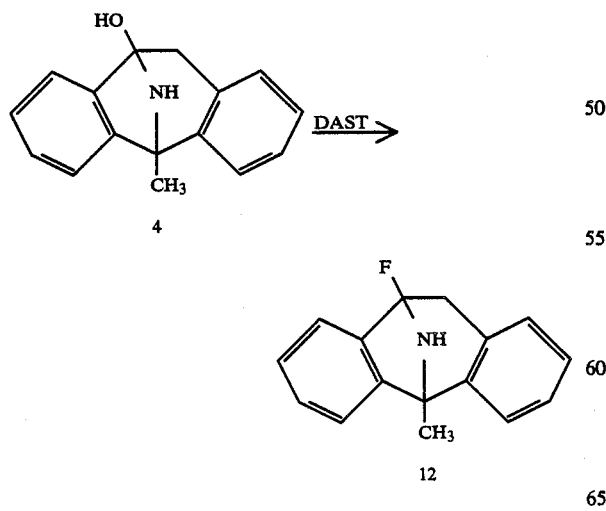

The isomeric 11-fluoro-MK-801 is prepared by treating the aziridine 5, with hydrogen fluoridepyridine (HF-70%; pyridine-30%) at about −90° to −60° C., preferably about −78° C. followed by spontaneous warming to ambient temperature (15° to 30° C.) at which it is maintained for about 12 to 36 hours in accordance with the following reaction.

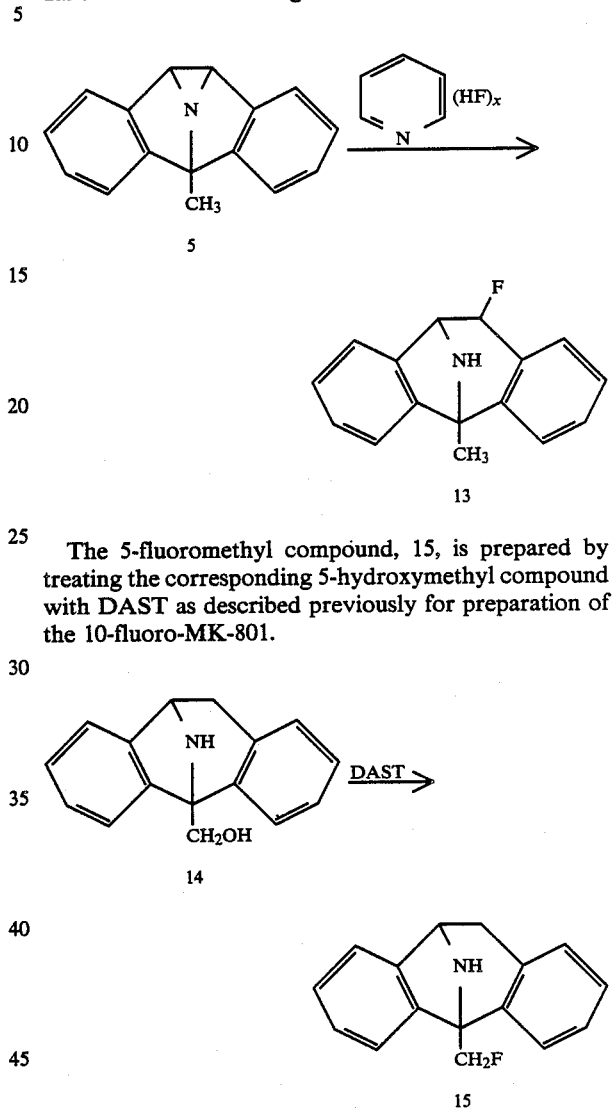

The 5-fluoromethyl compound, 15, is prepared by treating the corresponding 5-hydroxymethyl compound with DAST as described previously for preparation of the 10-fluoro-MK-801.

Alternatively it is prepared by slow addition of compound 16 to trifluoromethane sulfonic anhydride (TFMSA) in pyridine-methylene chloride at about −10° to +10° C. followed by stirring for about 15 minutes to 2 hours. The product from that reaction in an ethereal solvent such as THF or ether is added to a solution of tetra-n-butylammonium fluoride in an ethereal solvent and heated at reflux for about 1 to 4 hours.

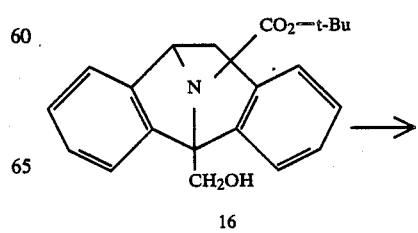

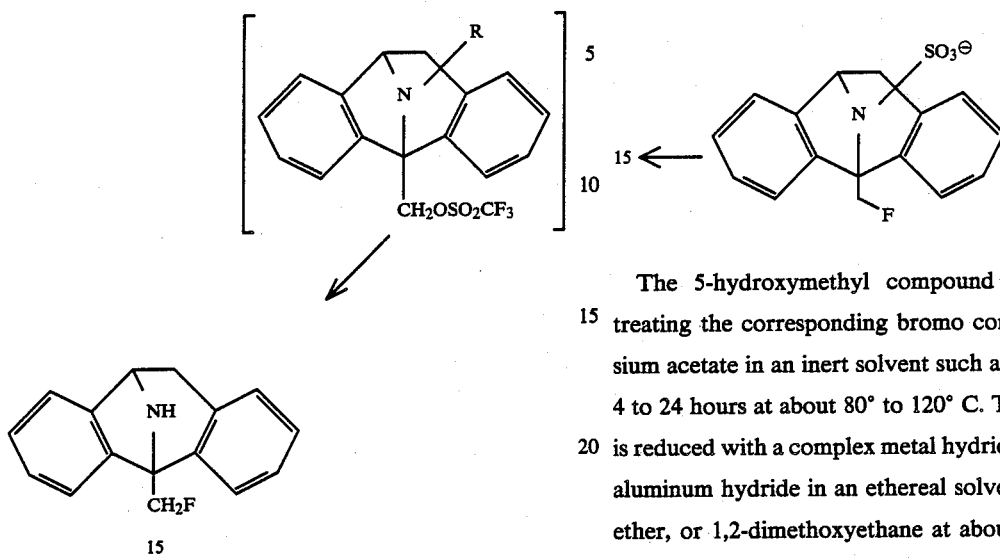

An additional procedure for preparing compound 15, comprises treating compound 14 with TFMSA in the presence of 2,6-di-t-butyl-4-methylpyridine in a chlorinated hydrocarbon solvent such as $CH_2Cl_2$ or $CHCl_3$ at about $-10°$ to $+10°$ C. for about 0.5 to 2 hours to obtain the N-trifluoromethylsulfonyl derivative 16a. Treatment of 16a with tetra-n-butylammonium fluoride in a polar solvent such as acetonitrile at about 10° to 30° C. for about 5 to 20 minutes followed by acidification with dilute acid provides the cyclic sulfamate 16b. Further treatment with tetra-n-butylammonium fluoride but at about 50°–90° C. for about 15 to 40 minutes provides the 5-fluoromethyl analog 15.

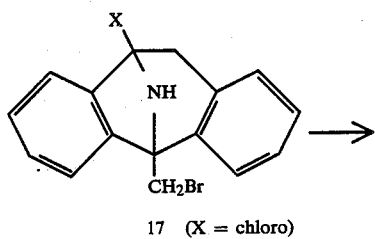

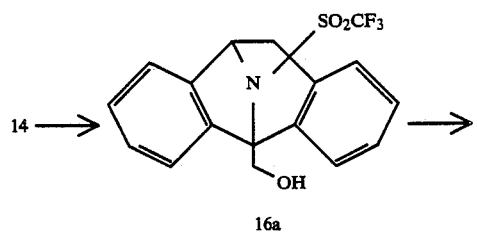

The 5-hydroxymethyl compound is prepared by treating the corresponding bromo compound with cesium acetate in an inert solvent such as DMF for about 4 to 24 hours at about 80° to 120° C. The ester product is reduced with a complex metal hydride such as lithium aluminum hydride in an ethereal solvent such as THF, ether, or 1,2-dimethoxyethane at about $-10°$ to $+10°$ C. for about 0.5 to 3 hours. The process may be depicted as follows:

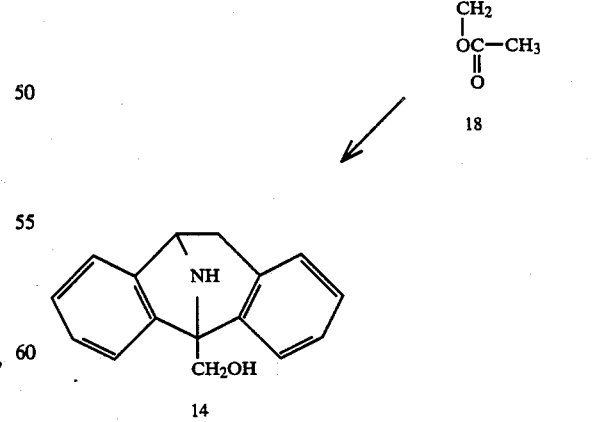

Alternatively, the 5-hydroxymethyl compound is prepared in accordance with the following reaction scheme:

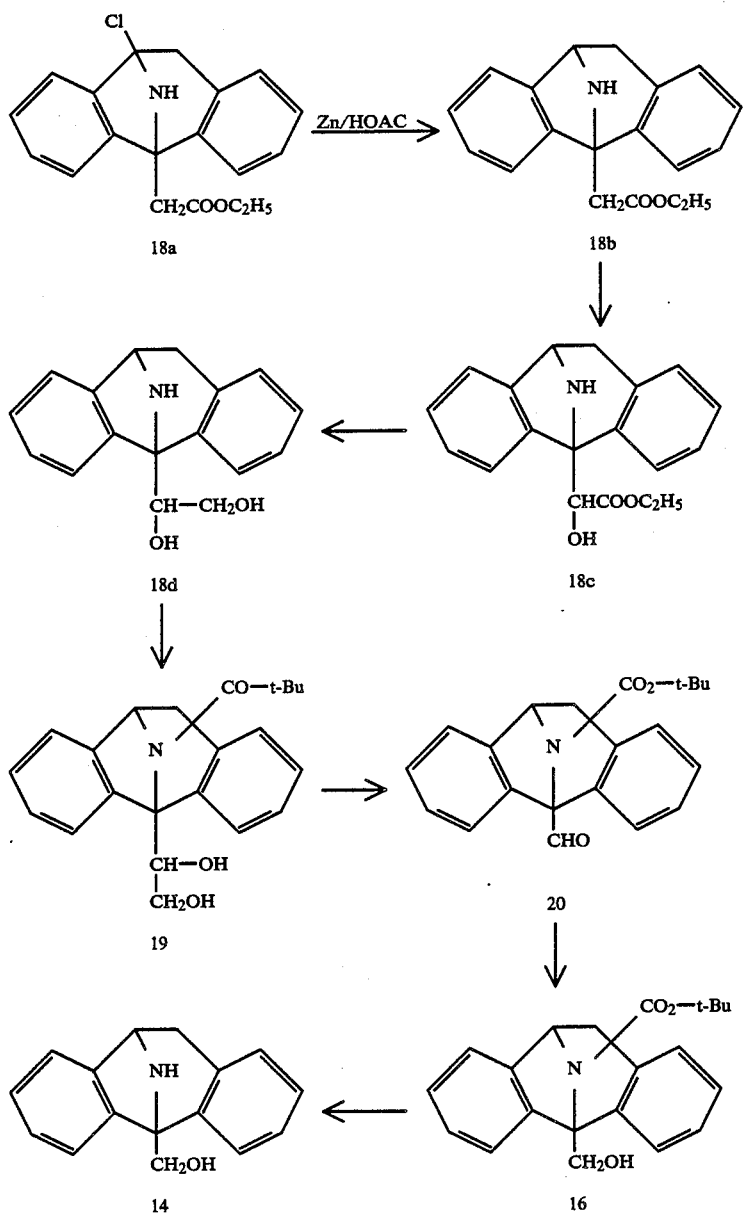

The chloro group in structure 18a is hydrogenolyzed by treatment with zinc acetic acid at about 40° to 70° C. for about 10 to 24 hours.

Compound 18c is prepared by treatment of 18b with potassium hexamethyldisilylamide at about −85° to −70° C. in an ethereal solvent such as diethyl ether or THF followed by treatment with 3-phenyl-2-benzenesulfonyloxaziridine at about −60° to −75° C. for about 20 to 50 minutes followed by quenching with a little dilute hydrochloric acid.

The dihydroxyethyl derivative, 18d is prepared by reduction of the ester group in 18c with a complex metal hydride such as LiAlH4 in an ethereal solution such as diethyl ether or THF or mixtures thereof at about 30° to 60° for about 1 to 3 hours. The t-butoxycarbonyl derivative 19 is then prepared by standard methods.

The diol 19 is oxidized with sodium metaperiodate in an aqueous solvent system such as aqueous dioxane at about 15° to 35° C. for about 1 to 6 hours. The resultant aldehyde 20 is then reduced to the carbonol 14 with a complex metal hydride such as sodium borohydride in basic aqueous alcoholic solution at about −5° to +5° C. followed by agitating at room temperature (15°-25° C.) for about 45 minutes to 3 hours.

The t-butoxycarbonyl protecting group is readily removed by standard procedures such as with trifluoracetic acid in a chlorinated hydrocarbon such as methylene dichloride at about −5° to +5° C. for about 0.5 to 2 hours.

A third method of preparing the 5-hydroxymethyl analog comprises treatment of a 5-phenylsulfinylmethyl compound with 2,6-lutidene and trifluoroacetic acid in a polar organic solvent such as acetonitrile at about −5° to +5° C. for about 0.25 to 2 hours followed by treatment with dilute alkali, preferably sodium hydroxide, and stirring about 4 to 10 hours at about ambient temperature. The intermediate sulfenate ester is then hydrolyzed with acid, preferably with Aq Hcl in THF.

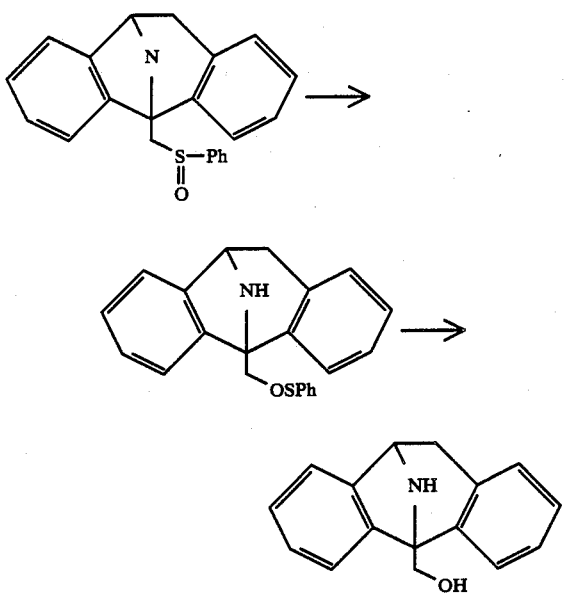

In the preparation of the 5-(2-fluoroethyl) compound the final step comprises treating the 5-(2-(t-butyldimethylsilyloxy)ethyl analog with tetra-n-butylammonium fluoride in an inert solvent such as acetonitrite at about 50°–80° C. for about 10–30 minutes followed by treatment with dilute HCl at about 50°–80° for about 10–30 minutes to remove the intermediate sulfonate group from the imino nitrogen.

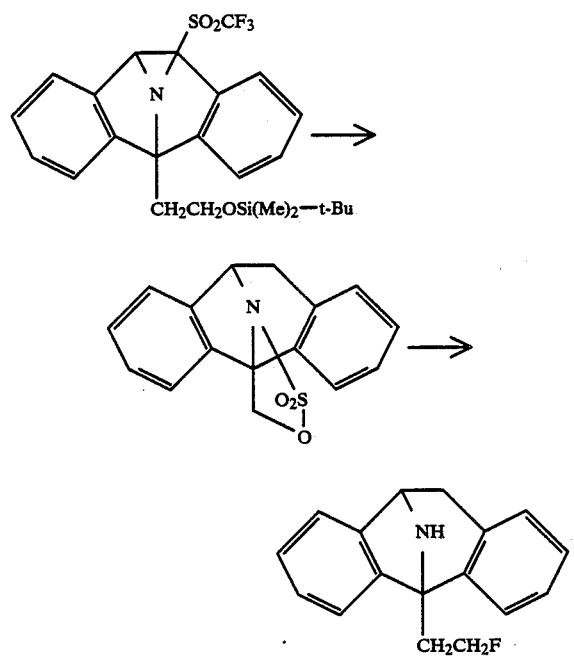

A 5-(2-hydroxyethyl)-10-hydroxy analog is prepared by lithium aluminum hydride reduction of the corresponding 5-carbethoxymethyl-10-hydroxy compound in substantially the same manner as described above for reduction of the ester 18c.

EXAMPLE 1

5-Methyl-10-hydroxyl-10,11-dihydro-5H-dibenzo[a,d]cyclohepten-5,10-imine

Step A: Preparation of E/Z-5-Thiophenylmethylidene-10-oxo-10,11-dihydro-5H-dibenzo[a,d]cycloheptene To a stirred solution of 3.25 g (12.5 mmol) of diethyl phenylthiomethylphosphonate in 7.0 mL of THF at 0° C. under $N_2$ was added 7.8 mL of a 1.6M solution of n-butyllithium dropwise via syringe. The solution was stirred at 0° C. for 45 minutes, followed by the dropwise addition of a solution of 3.04 g (10.0 mmol) of 10-(4'-methylpiperazin-1-yl)-5H-dibenzo[a,d]cyclohepten-5-one in 10.0 mL of THF via cannula. After stirring for 1 hour at 0° C., the solution was warmed to 22° C. over 45 minutes, and stored at −5° C. for 48 hours. The reaction mixture was poured into 200 mL of 5% HCl and stirred rapidly with 300 mL of $CHCl_3$ for 1 hour. The organic layer was worked up to give 5.3 g of a yellow foam which was chromatographed on 500 g of $SiO_2$ using $CHCl_3$ to give 2.14 g (65%) of product as a yellow foam. A small sample was crystallized from $CH_3OH$ to give a pale yellow solid. m.p. 203.5°–205° C.

Step B: Preparation of E/Z-5-Phenylsulfonylmethylidene-10-oxo-10,11-dihydro-5H-dibenzo[a,d]cycloheptene To a stirred solution of 3.07 g (14 mmol) of 85% metachloroperbenzoic acid in 240 mL of $CH_2Cl_2$ was added a solution of 2.14 g (6.52 mmol) of product from Step A in 36 mL of $CH_2Cl_2$ over a 15 minute period, followed by the addition of 100 mL of 5% $NaHCO_3$. After stirring rapidly for 5 hours, the organic layer was washed with 100 mL of 10% $Na_2SO_3$, 100 mL of 5% $NaHCO_3$, and dried over $MgSO_4$. The solvent was removed and the residue crystallized from 1:3 ethyl acetate-hexanes to afford 1.87 g (80%) of product as colorless needles: mp 180°–182.5° C.

Step C: Preparation of 5-Phenylsulfonylmethyl-N,10-dihydroxy-10,11-dihydro-5H-dibenzo[a,d]cyclohepten-5,10-imine To a stirred slurry of 1.87 g (5.2 mmol) of product from Step B in 200 mL of wet ether was added 0.80 g (11.5 mmol) of hydroxylamine hydrochloride and 1.60 g (11.8 mmol) of sodium acetate trihydrate. The mixture was stirred under $N_2$ for 16 hours and extracted with 200 mL of $CH_2Cl_2$. The organic layer was washed with 2% $NaHCO_3$, water, and twice with saturated NaCl solution, dried over $MgSO_4$ and the solvents removed to give 2.16 g (100%) of product as a colorless solid.

Step D: Preparation of 5-Phenylsulfonylmethyl-10-hydroxy-10,11-dihydro-5H-dibenzo[a,d]cyclohepten-5,10-imine A slurry of 2.16 g (5.2 mmol) of product from Step C in 60 mL of acetic acid was stirred with 3.2 g of Zn dust under $N_2$ for 3.5 hours. The mixture was filtered and the Zn washed with acetic acid. Evaporation of the solvent at reduced pressure gave a residue which was diluted with 150 mL of water and brought to pH 10 with 2.0M NaOH. The resulting precipitate was stirred in an ice bath for 30 minutes, filtered, and washed well with water. Drying at reduced pressure to constant weight afforded 2.01 g (>100%) of product as a colorless solid.

Step E: Preparation of 5-Methyl-10-hydroxy-10,11-dihydro-5H-dibenzo[a,d]cyclohepten-5,10-imine Approximately 100 mL of ammonia was passed through a KOH column and condensed at −78° C. into an oven dried 3-necked round bottom flask equipped with a magnetic stirrer, dry-ice condenser, and a gas inlet tube. To this solution was added 100 mg (14.4 mg atm) of washed (pentane/ethanol/ether) lithium wire in small pieces. After stirring the dark blue mixture for 30 minutes at −78° C., 0.25 mL of t-butanol was added, followed by the addition of 1.0 g (2.65 mmol) of product from Step D as a solid. The cold bath was removed, and the mixture allowed to reflux for 1.3 hours when an additional 50 mg (7.2 mg atm) of lithium wire was added. Refluxing was continued for an additional 3.7 hours, the mixture recooled to −78° C., and quenched carefully with saturated NH4Cl solution. The ammonia was allowed to evaporate by removing the condenser and cold bath for 1 hour. Extraction of the reaction mixture with 2×100 mL of CHCl3 and the usual workup gave a solid residue which was crystallized from 25 mL of CH3CN to give 383 mg (61%) of product as colorless crystals: m.p. 228°–231° C. dec.;

Anal Calc'd for $C_{16}H_{15}NO$: C, 80.98; H, 6.37; N, 5.90. Found: C, 80.96; H, 6.60; N, 5.99.

EXAMPLE 2

5-Methyl-10,11-Dihydro-11-endo-hydroxy-5H-dibenzo[a,d]cyclohepten-5,10-imine

Step A: Preparation of 8b,8c-dihydro-4b-methyl-4bH-aziridino[2,1,3-c,d]dibenzo[a,f]pyrrolizine A solution of 4 g of 5-methyl-5-methoxyamino-5H-dibenzo[a,d]cycloheptene[1] in 230 ml of dry tetrahydrofuran stirred under nitrogen and chilled to −78° C. in a dry ice/acetone bath was treated dropwise with 65 mL of 1.47M n-butyllithium in hexane. After stirring at −78° C. for 30 minutes the solution was allowed to warm to room temperature where it was stirred for 1 hour. The dark green solution was added to 100 mL of water, the organic layer was collected, and the aqueous layer was extracted with 2×100 mL of diethyl ether. The organic phases were combined, washed with saturated sodium chloride, dried over anhydrous sodium sulfate, filtered, and concentrated. The residue was triturated with hexane and chilled to give 13.6 g of 8b,8c-dihydro-4b-methyl-4bH-aziridino[2,1,3-c,d]dibenzo[a,f]pyrrolizine, m.p. 112°–114° C.

[1] Bender, U.S. Pat. No. 4,477,668.

Step B: Preparation of 5-methyl-10,11-dihydro-11-endo-acetoxy-5H-dibenzo[a,d]cyclohepten-5,10-imine 8b,8c-dihydro-4b-methyl-4bH-aziridino[2,1,3-c,d]dibenzo[a,f]pyrrolizine (8.6 g) was added to a warm solution of 40 g of sodium acetate in 100 mL of acetic acid and the mixture was stirred under reflux for 30 minutes. The reaction mixture was cooled in an ice bath and neutralized with concentrated ammonium hydroxide. The mixture was extracted with 4×200 mL of diethyl ether and the extract was washed with 2×100 mL of water and 2×50 mL of saturated sodium chloride, dried over anhydrous sodium sulfate, filtered, and concentrated to dryness. Purification by flash chromatography (silica gel, 230–400 mesh; methylene chloride (80%): diethyl ether (10%): acetone (8%): methanol (2%)) gives 7.9 g of 5-methyl-10,11-dihydro-11-endo-acetoxy-5H-dibenzo[a,d]cyclohepten-5,10-imine.

Step C: Preparation of 5-methyl-10,11-dihydro-11-endo-hydroxy-5H-dibenzo[a,d]cyclohepten-5,10-imine A solution of 10.6 g of 5-methyl-10,11-dihydro-11-endo-acetoxy-5H-dibenzo[a,d]cyclohepten5,10-imine (product from Step B) and 56 g potassium hydroxide pellets (5N) in 200 mL of dry methanol was stirred at room temperature for 3 hours. Concentration of the reaction mixture to dryness and trituration of the residue with 150 mL of water affords 9.0 g of crude product which on recrystallization from isopropanol gives 7.7 g of 5-methyl-10,11-dihydro-11-endo-hydroxy-5H-dibenzo[a,d]cyclohepten-5,10-imine, m.p. 189.5°–190.5° C.

EXAMPLE 3

10,11-Dihydro-11-exo-hydroxy-5H-5-methyl-dibenzo[a,d]cyclohepten-5,10-imine

Step A: Preparation of N-(carbo-tert-butoxy)-5-methyl-10,11-dihydro-11-endo-hydroxy-5H-dibenzo[a,d]cyclohepten-5,10-imine To a stirred solution of 2.2 g of 5-methyl-10,11-dihydro-11-endo-hydroxy-5H-dibenzo[a,d]cyclohepten-5,10-imine in 60 ml of tetrahydrofuran was added 60 mL 1N aqueous sodium hydroxide followed by 6 g of di-tert-butyl dicarbonate. The mixture was stirred under reflux for 1.5 hours and allowed to cool to room temperature. The organic phase was collected and the aqueous phase was extracted with 4×50 mL of diethyl ether. The combined organics were washed with water and saturated sodium chloride, dried over anhydrous sodium sulfate, and concentrated to dryness to give 3.6 g crude product which, after recrystallization from isopropanol, yielded 2.7 g of N-(carbo-tert-butoxy)-5-methyl-10,11-dihydro-11-endohydroxy-5H-dibenzo[a,d]cyclohepten-5,10-imine, m.p. 177°–178° C.

Step B: Preparation of N-(carbo-tert-butoxy)-5-methyl-10,11-dihydro-11-endo-methanesulfonyl-5H-dibenzo[a,d]cyclohepten-5,10-imine To an ice cold solution of 2.7 g N-(carbo-tert-butoxy)-5-methyl-10,11-dihydro-11-endo-hydroxy-5H-dibenzo[a,d]cyclohepten-5,10-imine in 30 mL dry methylene chloride under nitrogen was added 1.6 mL triethylamine followed by 0.67 mL methanesulfonyl chloride. The reaction mixture was stirred at 0° C. for 1 hour and then filtered through diatomaceous earth. The filtrate was washed with water and saturated sodium chloride, dried over anhydrous sodium sulfate, and concentrated to give 3.4 g crude N-(carbo-tert-butoxy)-5-methyl-10,11-dihydro-11-endo-methanesulfonyl-5H-dibenzo[a,d]cyclohepten-5,10-imine, m.p. 137° C. (darkens), 143° C. (d).

Step C: Preparation of N-(carbo-tert-butoxy)-5-methyl-10,11-dihydro-11-endo-acetoxy-5H-dibenzo[a,d]cyclohepten-5,10-imine and N-(carbo-tert-butoxy)-5-methyl-10,11-dihydro-11-exo-acetoxy-5H-dibenzo[a,d]cyclohepten-5,10-imine A mixture of 3.4 g N-(carbo-tert-butoxy)-5-methyl-10,11-dihydro-11-endo-methanesulfonyl-5H-dibenzo[a,d]cyclohepten-5,10-imine and 12.4 g of tetrabutylammonium acetate in 30 mL of dry 1-methyl-2-pyrrolidinone was heated in an oil bath at 140° C. under nitrogen for 2.5 hours. The mixture was added to 150 mL of water and the solution was extracted with 4×50 mL of methylene chloride. The extract was washed with water and saturated sodium chloride, dried over anhydrous sodium sulfate and concentrated to give 3.9 g of an oil. Flash chromatography (silica gel, 230–400 mesh; hexane (90%): ethyl acetate (10%)) afforded 2.1 g of a mixture of N-(carbo-tert-butoxy)-5-methyl-10,11-dihydro-11-endo-acetoxy-5H-dibenzo[a,d]-cyclohepten-5,10imine and N-(carbo-tert-butoxy)-5-methyl-10,11-dihydro-11-exo-acetoxy-5H-dibenzo[a,d]-cyclohepten-5,10-imine in a ratio of 3:2.

Step D: Preparation of N-(carbo-tert-butoxy)-5-methyl-10,11-dihydro-11-endo-hydroxy-5H-dibenzo[a,d]cyclohepten-5,10-imine and N-(carbo-tert-butoxy)-5-methyl-10,11-dihydro-11-exo-hydroxy-5H-dibenzo[a,d]cyclohepten-5,10-imine A mixture of 2.0 g of N-(carbo-tert-butoxy)-5-methyl-10,11-dihydro-11-endo-acetoxy-5H-dibenzo[a,d]-cyclohepten-5,10-imine and N-(carbo-tert-butoxy)-5-methyl-10,11-exo-acetoxy-5H-dibenzo[a,d]cyclohepten-5,10-imine in 40 mL methanol and 5.3 mL 1N aqueous potassium hydroxide was stirred at room temperature for 2 hours and concentrated to dryness. The residue was taken up in 50 mL of water and the mixture was extracted with 4×25 mL of methylene chloride. The combined methylene chloride extracts were washed with water and saturated sodium chloride, dried over anhydrous sodium sulfate, and concentrated to give 1.7 g crude product as an oil. Purification by flash chromatography (silica gel, 230–400 mesh; chloroform (95%): diethyl ether (5%)) gives 1.3 g of a mixture of N-(carbo-tert-butoxy)-5-methyl-10,11-dihydro-11-endo-hydroxy-5H-dibenzo[a,d]cyclohepten-5,10-imine and N-(carbo-tert-butoxy)-5-methyl-10,11-dihydro-11-exo-hydroxy-5H-dibenzo[a,d]cyclohepten-5,10-imine in a ratio of 5:1 and 0.4 g of an ortho-carbonate side product derived from the exo-alchol.

Step E: Preparation of 5-methyl-10,11-dihydro-11-endo-hydroxy-5H-dibenzo[a,d]cyclohepten-5,10-imine and 5-methyl-10,11-dihydro-11-exo-hydroxy-5H-dibenzo[a,d]cyclohepten-5,10-imine Ethanolic HCl (14 mL, 6.2M) was added to an ice cooled solution of 1.2 g of N-(carbo-tert-butoxy)-5-methyl-10,11-dihydro-11-endo-hydroxy-5H-dibenzo[a,d]cyclohepten-5,10-imine and N-(carbo-tert-butoxy)-5-methyl-10,11-dihydro-11-exo-hydroxy-5H-dibenzo-[a,d]cycloheptene-5,10-imine in 40 mL of absolute ethanol. The ice-bath was removed and stirring was continued at room temperature overnight. The reaction mixture was concentrated and the residue was dissolved in 50 mL of water. The solution was made slightly basic by the addition of dilute ammonium hydroxide and was extracted with methylene chloride. The combined methylene chloride extracts were washed with saturated sodium bicarbonate and saturated sodium chloride, dried over anhydrous sodium sulfate, and concentrated to give 0.6 g of crude product as an oil. The product was purified by flash chromatography (silica gel, 230–400 mesh; chloroform (95%): methanol (5%)) to give 0.4 g of a mixture of 5-methyl-10,11-dihydro-11-endo-hydroxy-5H-dibenzo[a,d]-cyclohepten-5,10-imine and 5-methyl-10,11-dihydro-11-exo-hydroxy-5H-dibenzo[a,d]cyclohepten-5,10-imine. The epimeric alcohols were separated by preparative HPLC [Spectra-Physics system; Whatman Partisil M20 10/25 ODS-3; acetonitrile (10%): methanol (10%): water (80%)] to give 320 mg of 5-methyl-10,11-dihydro-11-endo-hydroxy-5H-dibenzo[a,d]-cyclohepten-5,10-imine, m.p. 189.5°–190.5° C., $^1$H NMR (300 mHz) (CDCl$_3$) δ: 1.90 (s, 3H, CH$_3$), 4.69 (d, 1H, J=5.8 Hz, C$_{10}$ C—H), 5.13–5.17 (m, 1H, C$_{11}$ C—H), 7.10–7.41 (m, 8H, Ar)] and 42 mg of 5-methyl-10,11-dihydro-11-exo-hydroxy-5H-dibenzo[a,d]cyclohepten-5,10-imine which, on recrystallization from ethyl acetate:hexane, has m.p. 190° C. (d), $^1$H NMR (300 mHz) (CDCl$_3$) δ: 2.12 (s, 3H, CH$_3$), 4.63 (s, 1H, C$_{10}$ C—H), 5.02 (s, 1H, C$_{11}$ C—H), 7.07–7.39 (m, 8H, Ar).

EXAMPLE 4

5-Methyl-10,11-dihydro-11-exo-hydroxy-5H-dibenzo[a,d]cyclohepten-5,10-imine

Step A: Preparation of N-(carbo-tert-butoxy)-5-methyl-10,11-dihydro-11-oxo-5H-dibenzo[a,d]cyclohepten-5,10-imine To a stirred solution of 0.76 mL oxalyl chloride in 20 mL of dry methylene chloride cooled to −60° C. in a dry ice/chloroform bath and under nitrogen was added a solution of 1.2 mL dry dimethylsulfoxide in 4 mL dry methylene chloride. The reaction mixture was stirred at −60° C. for 2 minutes and a solution of 2.7 g N-(carbo-tert-butoxy)-5-methyl-10,11-dihydro-11-endo-hydroxy-5H-dibenzo[a,d]cyclohepten-5,10-imine in 15 mL dry methylene chloride and 1.5 mL dry dimethyl sulfoxide was added dropwise. The reaction mixture was stirred at −60° C. for 20 minutes and 5.5 mL triethylamine was added. Stirring at −60° C. was continued for 10 minutes after which the cooling bath was removed and the mixture was allowed to warm to room temperature. To the reaction mixture was added 10 mL water; the organic layer was collected and the aqueous layer was extracted with 2×40 mL of methylene chloride. The combined organic phases were washed with 1×50 mL of 1% aqueous HCl, 1×50 mL of water, 1×50 ml of 5% aqueous sodium carbonte, 1×50 mL of water, and 2×50 mL of saturated sodium chloride, dried over anhydrous sodium sulfate, and concentrated to dryness to give 2.6 g of product which, after recrystallization from isopropanol, yielded 2.4 g of N-(carbo-tert-butoxy)-5-methyl-10,11-dihydro-11-oxo-5H-dibenzo[a,d]cyclohepten-5,10-imine, m.p. 124°–126° C.

Step B: Preparation of 10,11-dihydro-11-endo-hydroxy-hydroxy-5H-dibenzo[a,d]cyclohepten-5,10-imine and 5-methyl-10,11-dihydro-11-exo-hydroxy-5H-dibenzo[a,d]cyclohepten-5,10-imine To a solution of 0.3 g N-(carbo-tert-butoxy)-5-methyl-10,11-dihydro-11-oxo-5H-dibenzo[a,d]cyclohepten-5,10-imine in 3 mL dry tetrahydrofuran cooled to −78° C. in a dry ice/acetone bath and under argon was added dropwise 4.4 mL of a 1.0M solution of diisobutylaluminum hydride in methylene chloride. After stirring at −78° C. for 1.5 hours the reaction mixture was cautiously quenched by the addition of 1 mL of methanol and allowed to warm to room temperature. The mixture was diluted with 20 mL of 0.5M aqueous sodium potassium tartrate, the organic phase was collected, and the aqueous phase was extracted with 2×10 mL of methylene chloride. The combined organic layers were washed with 3×20 mL of 0.5M aqueous sodium potassium tartrate and 2×20 mL of saturated sodium chloride, dried over anhydrous sodium sulfate, and concentrated to dryness to give 0.23 g of N-(carbo-tert-butoxy)-5-methyl-10,11-dihydro-11-endo-hydroxy-5H-dibenzo[a,d]cyclohepten-5,10-imine and N-(carbo-tert-butoxy)-5-methyl-10,11-dihydro-11-exo-hydroxy-5H-dibenzo-[a,d]cyclohepten-5,10-imine in a ratio of 2:1, respectively. These were deprotected and separated by preparative HPLC as described in Example 3, Step E.

EXAMPLE 5

10,11-Dihydro-5H-11-exo-hydroxy-5-methyldibenzo[a,d]cyclohepten-5,10-imine

Step A: Preparation of 11-t-Butylcarbamoyl-10,11-dihydro-10-hydroxy-dibenzo[a,d]cycloheptenone To a stirred mixture of 20.0 g (115 mmol) of N-chloro-N-sodio-t-butylcarbamate in 312 mL of $CH_3CN$ was added 20.55 g (121 mmol) of $AgNO_3$ and the mixture stirred for 10 minutes. Then 15.84 g (77 mmol) of dibenzosuberanone, 7.8 mL (0.8 mmol) of a solution of 2.5% $OsO_4$ in t-butanol, and 6.3 mL of water was added to the mixture. After stirring for 18 hours, an additional 1.3 mL of the $OsO_4$ solution was added, followed by 16.6 g (63.5 mmol) of tetraethylammonium acetate hydrate, and stirring continued for 22 hours. Then 1 mL of brine was added, the mixture filtered, and the filtrate refluxed with 154 mL of 5% aq. $Na_2SO_3$ for 4 hours. The mixture was cooled, filtered and evaporated at reduced pressure to remove most of the $CH_3CN$. The residue was diluted with 500 mL of water, extracted with 2×250 mL of $CHCl_3$, and the combined organic layers washed three times with water and dried over $MgSO_4$. Evaporation gave an oil which was chromatographed on 700 g of silica gel using 1:3 ethyl acetate-hexanes to afford 12 g of a yellow foam which was triturated with 1:2 ethyl acetate-hexanes to yield 6.66 g (26%) of title compound as pale yellow crystals: m.p., NMR, and IR did not contraindicate the assigned structure.

Anal. Calc'd for $C_{20}H_{21}NO_4$: C, 70.78; H, 6.24; N, 4.13.

Found: C, 70.87; H, 6.12; N, 4.10.

Step B: Preparation of 11-t-Butylcarbamoyl-10,11-dihydro-10-hydroxy-5-methyl-5H-dibenzo[a,d]cycloheptene To a stirred solution of 640 mg (1.89 mmol) of product from Step A in 15 mL of THF under $N_2$ at 0° C. was added 6.0 mL (8.4 mmol) of a solution of methyllithium (1.4M in ether) dropwise over a 5 minute period. The reddish solution was stirred in the cold for 2.0 hours, poured into ice-water and extracted with 3×50 mL of $CHCl_3$. The combined organic layers were washed with water and worked up as usual to give 690 mg of title compound as a colorless solid. An analytical sample was obtained by crystallization from 1:3 ethyl acetate-cyclohexane: m.p., NMR and IR did not contraindicate the assigned structure.

Anal. Calc'd for $C_{21}H_{25}NO_4$: C, 70.96; H, 7.09; N, 3.94.

Found: C, 70.77; H, 7.16; N, 4.10.

Step C: Preparation of N-t-Butoxycarbonyl-10,11-dihydro-11-exo-hydroxy-5-methyl dibenzo[a,d]cyclohepten-5,10-imine.

A stirred mixture of 1.25 g (3.5 mmol) of product from Step B in 200 mL of benzene was heated to 50° C., followed by the addition of 50 mg of p-toluenesulfonic acid hydrate. After stirring for 5.5 hours, the reaction was quenched with 5% $NaHCO_3$, diluted with 100 mL of $CHCl_3$, and the organic layer washed with 5% $NaHCO_3$, brine, and worked up in the usual manner to give 1.2 g of an oil which was used directly in the next reaction. A small sample was chromatographed on silica gel using 1:3 ethyl acetatehexanes and crystallized from cyclohexane. NMR, IR, and ANAL did not contraindicate the assigned structure.

Step D: Preparation of 10,11-dihydro-5H-11-exo-hydroxy-5-methyl-dibenzo[a,d]cyclohepten-5,10-imine A solution of 1.2 g of crude product from Step C in 60 mL of $CHCl_3$ was cooled to 0° C. and 30 mL of trifluoroacetic acid was added in one portion. After stirring for 2.0 hours in the cold, the solvents were removed at reduced pressure, the residue treated with 5% $NaHCO_3$ and extracted with 2×100 mL $CHCl_3$. The combined organic layers were washed with water and worked up in the usual way to give a brown oil which was chromatographed on 60 g of silica gel using 95:5:0.5 $CHCl_3$—$CH_3OH$—$NH_4OH$ to afford 210 mg of title compound as a colorless solid after crystallization from 1:1 ethyl acetate-hexanes: m.p., NMR and IR did not contraindicate the assigned structure.

Anal. Calc'd for $C_{16}H_{15}NO$: C, 80.98; H, 6.37; N, 5.90.

Found: C, 80.66; H, 6.48; N, 5.96.

EXAMPLE 6

5-Methyl-10-fluoro-10,11-dihydro-5H-dibenzo[a,d]cyclohepten-5,10-imine

To a stirred solution of 232 µL (306 mg, 1.90 mmol) of diethylaminosulfurtrifluoride (DAST) in 2.0 mL of $CH_2Cl_2$ was added 150 mg (0.63 mmul) of 5-methyl-10-hydroxy-10,11-dihydro-5H-dibenzocyclohepten-5,10-imine in 9.0 mL of $CHCl_3$ as rapidly as possible under $N_2$ and rinsed with 1.0 mL of $CH_2Cl_2$. After stirring for 30 minutes, an additional 77 µL (0.63 mmol) of DAST was added dropwise and stirring continued for 15 minutes. The reaction mixture was poured into ice-5% $NaHCO_3$, extracted with $CHCl_3$, and worked up to give an amber oil which was chromatographed on 25 g of 240-400 mesh $SiO_2$ using $CHCl_3$ to apply the sample and 1:4 ethyl acetate-hexanes as the eluant. The pure fractions were combined and evaporated to afford a solid which was crystallized from 1:3 ethyl acetate-hexanes to yield 100 mg of product as colorless crystals: mp 138°-140° C.

Anal. Calc'd for: $C_{16}H_{14}FN$: C, 80.31; N, 5.90; N, 5.85.

Found: C, 80.15; H, 6.10; N, 5.85.

EXAMPLE 7

10,11-Dihydro-11-fluoro-5-methyl-5H-dibenzo[a,d]cyclohepten-5,10-imine

Hydrogen fluoride-pyridine (ca. 10 mL) was cooled under $N_2$ in a dry ice-acetone bath and [(4b,4c-dihydro-8BH-azirino[2,1,3-cd]dibenzo[a,f]pyrrolizen-8b-yl)]methane (See Example 2, Step A) (197 mg, 0.9 mmol) was added. The mixture was allowed to warm to room temperature and stirred for 18 hours. Chloroform (100 mL) was added to the mixture then ice. The pH of the aqueous layer was adjusted to about 10, the mixture was filtered to remove the solids and the layers were separated. The organic layer was dried over $Na_2SO_4$ and evaporated to dryness in vacuo.

The product was purified by chromatography on silica gel by successively eluting with $CHCl_3$, $CHCl_3$—$CH_3OH$ (99:1 then 97.5-2.5) and $CHCl_3$—$CH_3OH$—$H_2O$ (95-5-0.5). The product-containing fractions were pooled, evaporated and rechromatographed on silica gel in $CHCl_3$—$CH_3OH$-acetic acid yielding 80 mg of product. The $^1H$—NMR was consistent with the structure of the intended product.

EXAMPLE 8

10,11-dihydro-5-hydroxymethyl-5H-dibenzo[a,d]cyclohepten-5,10-imine

Step A: Preparation of 10-Chloro-5-carboxymethyl-10,11-dihydro-5H-dibenzo[a,d]cyclohepten-5,10-imine To a stirred solution of 6.0 g (16.5 mmol) of 10-chloro-5-ethoxycarbonylmethyl-10,11-dihydro-5H-dibenzo[a,d]cyclohepten-5,10-imine in 333 mL of 1,2-dimethoxyethane (DME) was added a solution of 4.15 g (98.8 mmol) of LiOH*$H_2O$ in 67 mL of water dropwise under $N_2$. After stirring for 26 hours, 50 mL of 2.0M HCl was added, and the solution concentrated to remove the DME. To the resulting solution was added 50 mL of $CH_3CN$, and then diluted to 500 mL with water. This solution was purified on reversed phase HPLC (Waters Prep Pac C-18) using a 1.0% acetic acid-$CH_3CH$ gradient. Fractions containing substantial amounts of product as indicated by analytical HPLC were combined and evaporated to give 3.56 g (72%) of product as a pale yellow solid.

Anal. Calc'd for $C_{17}H_{14}ClNO_2$: C, 68.12; H, 4.71; N, 4.67.

Found: C, 68.04; H, 4.91; N, 4.35.

Step B: Preparation of 5-Bromomethyl-10-chloro-10,11-dihydro-5H-dibenzo[a,d]cyclohepten-5,10-imine To a refluxing slurry of 39 mg (0.13 mmol) of product from Step A and 20 mg (0.09 mmol) of HgO in 4.0 mL of $CCl_4$ was added 0.007 mL (0.13 mmol) of $Br_2$ in the dark. After refluxing for 1 hour, an additional 25 mg (0.12 mmol) of HgO and 0.008 mL of $Br_2$ were added, and refluxing continued for 6 hours in the dark. The mixture was diluted with $CH_2Cl_2$ and evaporated to dryness to give the product as an amber oil.

Step C: Preparation of 5-Acetoxymethyl-10-chloro-10,11-dihydro-5H-dibenzo[a,d]cyclohepten-5,10-imine A degassed solution of crude product from Step B in 5.0 mL of DMF was treated with 0.5 g of cesium acetate for 15 hours at 100° C. The solvents were removed at reduced pressure, and the residue worked up with water, extracted with $CHCl_3$, the organic layer was washed with water and dried over $Na_2SO_4$. Evaporation of the solvent at reduced pressure gave 9 mg (22%) of product as an amber oil.

Step D: Preparation of 10,11-Dihydro-5-hydroxymethyl-5H-dibenzo[a,d]cyclohepten-5,10-imine To a stirred solution of 9 mg (0.03 mmol) of product from Step C in 10 mL of ether at 0° C. was added 94 mg (2.5 mmol) of lithium aluminum hydride under $N_2$. After stirring for 1 hour at 0° C., there were added 0.094 mL of water, 0.094 mL of 15% NaOH, and 0.282 mL of water very carefully. The mixture was treated with $Na_2SO_4$, filtered, and the filtrate evaporated to dryness to give a residue which was purified by preparative TLC (Analtech silica gel) using 95:5:0.5 $CHCl_3$—$CH_3OH$—$NH_4OH$ to afford 4 mg (51%) of product as a colorless solid, m.p. 226°–228° C.

EXAMPLE 9

5-Hydroxymethyl-10,11-dihydro-5H-dibenzo[a,d]cyclohepten-5,10-imine

Step A: Preparation of 10,11-Dihydro-10-hydroximino-5-(E/Z)phenylthiomethylidene-5H-dibenzo[a,d]cycloheptene To a solution of 40.0 g (97.4 mmol) of 10-(4-methylpiperazinyl)-5H-5-phenylthiomethylidenedibenzo[a,d]cycloheptene in 1.0 L of methanol was added 34.2 g (492 mmol) of hydroxylamine hydrochloride, and the mixture heated at reflux for 2.5 hours. After cooling to ambient temperature, the reaction was concentrated at reduced pressure to remove most of the methanol, poured into 300 mL of water and extracted with $3 \times 200$ mL of $CHCl_3$. The combined organic layers were washed with water, brine, and worked up to give a foam which was crystallized from a small volume of methanol to give 34.5 g (95%) of title compound as colorless crystals: m.p. 134°–135° C.

Anal. Calc'd for $C_{22}H_{17}NOS$ C, 76,94; H, 4.99; N, 4.08.

Found: C, 77.27; H, 5.20; N, 3.96.

Step B: Preparation of 10,11-Dihydro-10-hydroxamino-5-(E/Z)phenylthiomethylidene-5H-dibenzo[a,d]cycloheptene To a stirred slurry of 7.85 g (22.9 mmol) of product from Step A in 150 mL of methanol precooled in an ice water bath was added 3.0 g (45.7 mmol) of sodium cyanoborohydride ($NaCNBH_3$) and a trace of methyl orange indicator. A solution of 1:1 methanol-con. HCl was added dropwise as required to maintain a strong pink color. After 2.0 hours, an additional 0.5 g (7.62 mmol) of $NaCNBH_3$ was added, and the mixture stirred in the cold for an additional 1.5 hours. The reaction mixture was made basic with 5% NaOH, and most of the solvent was removed at reduced pressure. The residue was partitioned between saturated $NaHCO_3$ and $CHCl_3$, the aqueous layer extracted with $2 \times 200$ mL of $CHCl_3$, and the combined organic layers washed with saturated $NaHCO_3$, water, and brine. Normal workup gave 8.5 g (100%) of title compound as a yellow foam: HRMS 345.118668—theory 345.118736.

Step C: Preparation of 10,11-Dihydro-N-hydroxy-5-phenylthiomethyl-5H-dibenzo[a,d]cyclohepten-5,10-imine A solution of 32.1 g (92.8 mmol) of product from Step B in 500 mL of toluene was heated at reflux for 5.0 hours, cooled and the solvent removed to afford 31.0 g of title compound as a yellow foam. Trituration with

Step D: Preparation of 10,11-Dihydro-5-phenylthiomethyl-5H-dibenzo[a,d]cyclohepten-5,10-imine A stirred mixture of 30.0 g (88.0 mmol) of product from Step C and 29.3 g (448 mmol) of Zn dust in 500 mL of glacial acetic acid was heated at 60° C. for 5.0 hours, filtered through a pad of filter aid and most of the solvent removed in vacuo. The residue was diluted with ice water, basified to pH 12 with 1.0M NaOH, and extracted with 3×200 mL of CHCl$_3$. The combined organic layers were washed with water and worked up in the usual fashion to give a yellow oil which was dissolved in 300 mL of ether. To this vigorously stirred solution was added 9.2 mL of 8.5M ethanolic HCl, and the resulting precipitate was collected to 23.2 g (74%) of title compound as its HCl salt: m.p. 284° C.

Anal. Calc'd for $C_{22}H_{19}NS \cdot HCl$: C, 72.21; H, 5.51; N, 3.83.

Found: C, 72.45; H, 5.89; N, 4.02.

Step E: Preparation of 10,11-Dihydro-5-phenylsulfinylmethyl-5H-dibenzo[a,d]cyclohepten-5,10-imine After cooling a solution of 468 mg (1.42 mmol) of product from Step D as its free base in 47 mL of CH$_2$Cl$_2$ to −78° C., 307 mg (1.4 mmol) of 80–85% m-chloroperbenzoic acid was added as a solid in one portion. The solution was stirred in the cold for 20 minutes and quenched with 25 mL of 10% Na$_2$SO$_3$ and diluted with saturated NaHCO$_3$. The aqueous layer was extracted with CH$_2$Cl$_2$ and the combined organic layers were washed with water, and worked up as usual to yield 466 mg (95%) of title compound as a colorless foam. An analytical sample was obtained by trituration with 1:1 ether-hexanes as colorless crystals.

Anal. Calc'd for $C_{22}H_{19}NOS$: C, 76.49; H, 5.54; N, 4.05.

Found: C, 76.23; H, 5.35; N, 4.17.

Step F: Preparation of 10,11-Dihydro-5-hydroxymethyl-5H-dibenzo[a,d]cyclohepten-5,10-imine To a stirred solution of 1.37 g (3.9 mmol) of product from Step E and 1.2 mL (9.88 mmol) of 2,6-lutidine in 25 mL of CH$_3$CN at 0° C. was added 1.4 mL (9.88 mmol) of trifluoroacetic anhydride dropwise. After stirring for 30 minutes, 20 mL of 5% NaOH was added, and the mixture stirred at ambient temperature for 6.0 hours. The mixture was extracted with CHCl$_3$, the organic layers washed with water, dried, and the solvents removed at reduced pressure. The residue was triturated with hexanes to provide 986 mg of a tan solid.

A solution of 960 mg of the solid in 15 mL of THF was stirred with 15 mL of 3.0M HCl for 16 hours, basified with 5% NaOH, and extracted with CHCl$_3$. The organic layer was washed with water, dried over Na$_2$SO$_4$ and the solvents removed at reduced pressure to give a residue which was crystallized from 4:1 ethyl acetate-hexanes to give 387 mg of title compound as a colorless solid. Crystallization from ethyl acetate provided an analytical sample.

Anal. Calc'd for $C_{16}H_{15}NO$: C, 80.98; H, 6.37; N, 5.90.

Found: C, 80.76; H, 6.66; N, 6.27.

EXAMPLE 10

10,11-Dihydro-5-hydroxymethyl-5H-dibenzo[a,d]cyclohepten-5,10-imine

Step A: Preparation of 5-Ethoxycarbonylmethyl-10,11-dihydro-5H-dibenzo[a,d]cyclohepten-5,10-imine A mixture of 5 g of 10chloro-5-ethoxycarbonylmethyl-10,11-dihydro-5H-dibenzo[a,d]cyclohepten-5,10-imine hydrochloride and 15 g of zinc dust in 60 mL of glacial acetic acid was stirred at 60° C. under a nitrogen atmosphere for 18 hours. The mixture was filtered through a pad of filter aid, the solids washed with acetic acid, and the filtrate carefully made basic with sodium bicarbonate. The aqueous mixture was extracted 3 times with CH$_2$Cl$_2$, the organic phases were combined and washed with water and brine, dried, and concentrated to afford 5-ethoxycarbonylmethyl-10,11-dihydro-5H-dibenzo[a,d]cyclohepten-5,10-imine in quantitative yield: $^1$H NMR (300 MHz) (CDCl$_3$) δ: 1.20 (t, 3H, J=6Hz, ester CH$_3$), 2.70 (d, 1H, J=18Hz, benzylic CH$_2$ endo), 3.44 (dd, 1H, J=18, 6Hz, benzylic CH$_2$, exo), 3.45 (ABq, 2H, J=18Hz, DMAB=79Hz, —CH$_2$CO$_2$Et), 4.11 (ABq, 2H, J=7.5Hz, DMAB=13Hz, ester CH$_2$), 4.76 (d, 1H, J=6Hz, methine), 6.90–7.33 (m, 8H, aryl).

Step B: Preparation of 5R-(1-Ethoxycarbonyl-1-hydroxy-12R)methyl-10,11-dihydro-5H-dibenzo[a,d]cyclohepten-5,10-imine A solution containing 15 mL (9.7 mmole) of potassium hexamethyldisilylamide (0.653M in toluene) in 40 mL of tetrahydrofuran (freshly distilled over benzophenone ketyl) was stirred under a nitrogen atmosphere at −78° C. while a solution of 1.1 g (3.7 mmole) of 5-ethoxycarbonylmethyl-10,11-dihydro-5H-dibenzo[a,d]cyclopheten-5,10-imine in 15 mL of dry tetrahydrofuran was added dropwise. When the addition was complete a solution of 3-phenyl-2-benzenesulfonyloxaziridine in tetrahydrofuran (2.5 g (9.5 mmole) in 10 mL) was injected into the reaction mixture through a septum. The resulting yellow solution was stirred at −60° C. to −75° C. for 30 minutes after which the reaction was quenched by the addition of 5 mL of 6N hydrochloric acid. Tetrahydrofuran was removed on a rotary evaporator and the residue was dissolved in water. This acidic aqueous solution was extracted twice with ethyl acetate and then the aqueous phase was made alkaline with sodium bicarbonate and extracted four times with ethyl acetate. The latter organic extracts were combined, washed with dilute aqueous sodium bicarbonate, brine, and then dried over sodium sulfate. Removal of the solvent left 820 mg of the title compound as a crystalline white solid, m.p. 145°–146° C.

Step C: Preparation of 5-(1,2-Dihydroxyethyl)-10,11-dihydro-5H-dibenzo[a,d]cyclohepten-5,10-imine The α-hydroxyester product from Step B (2.39 g, 7.75 mmole), dissolved in a mixture of ether (15 mL) and freshly distilled tetrahydrofuran (40 mL), was added dropwise under a nitrogen atmosphere to a suspension of lithium aluminum hydride (400 mg, 10.5 mmole) in 60 mL of dry ether at 50° C. After two hours the reaction was complete by tlc (silica GF, CHCl$_3$, CH$_3$OH, NH$_4$OH; 95:5:0.5). The mixture was cooled in an ice bath. A saturated sodium sulfate solution in water (10 mL) was added dropwise, and the resulting mixture was stirred at 25° C. for several hours. The ethereal solution was decanted and the solid residue was extracted several times with chloroform. The organic solutions were combined, evaporated to dryness, and the residue was re-dissolved in a chloromdichloromethane mixture. The solution was washed twice with brine, dried over magnesium sulfate, and evaporated to give 1.65 g of 5-(1,2-dihydroxyethyl)-10,11-dihydro-5H-dibenzo[a,d]cyclohepten-5,10-imine. An analytical sample was recrystallized from acetonitrile; m.p. 191°–193.5° C.

Step D: Preparation of N-tert-Butoxycarbonyl-5-(1,2-dihydroxyethyl)-10,11-dihydro-5H-dibenzo[a,d]cyclohepten-5,10-imine A solution of 3.95 g (14.8 mmole) 5-(1,2-dihydroxyethyl)-10,11-dihydro-5H-dibenzo[a,d]cyclohepten-5,10-imine in 100 mL of tetrahydrofuran was treated first with 75 mL of a 1N sodium hydroxide solution, followed by 16.3 g (75 mmol) of di-tert-butyldicarbonate. The resulting mixture was stirred under nitrogen at 40°–45° C. for 18 hours, then at 25° C. for 24 hours. The mixture was concentrated in vacuo, the residue taken up in dichloromethane, and the solution washed twice with water, then the brine. After removal of the solvent there remained an oil which was chromatographed (flash-CHCl$_3$, CH$_3$OH, NH$_4$OH; 95:5:0.5) to afford, after elution of a by-product, 4.6 g of the title compound: $^1$H NMR (300 MHz) (CHCl$_3$) δ: 1.37 (s, 9H, CH$_3$), 2.0 (broad s, 1H, OH), 2.55 (d, 1H, J=17Ha, benzylic CH$_2$, endo), 3.40–3.70 (m, 3H, benzylic CH$_2$, exo, and CH$_2$OH), 4.05 (m, 1H, CHOH), 5.26 (d, 1H, J=6Hz, bridgehead methine), 5.46 (broad s, 1H, OH), 6.87–7.30 (m, 6H, aryl), 7.90 (d, 1H, J=6Hz, aryl), 8.06 (m, 1H, aryl).

Step E: Preparation of N-tert-Butoxycarbonyl-5-formyl-10,11-dihydro-5H-dibenzo[a,d]cyclohepten-5,10-imine To a solution of the N-BOC diol of Step D (4.6 g, 12.5 mmole) in 100 mL of dioxane was added a solution containing 8.6 g (40 mmole) sodium metaperiodate in 75 mL of water. After 3 hours at 25° C. the reaction was complete by tlc (Silica GF; CHCl$_3$, CH$_3$OH, NH$_4$OH, 95:5:0.5). The solid was removed by filtration and washed several times with fresh dioxane. The combined filtrates were concentrated in vacuo to a slurry which was extracted three times with toluene. The combined toluene extracts were washed with water, then with brine, dried over sodium sulfate, and evaporated to dryness, leaving 3.15 g of a waxy solid which is tlc homogeneous. Infrared (C—H stretch at 2835, 2760 cm$^{-1}$; C=O at 1740, 1715 cm$^{-1}$) and pmr (CHO at 9.83 and 9.96 ppm) spectra confirm the title compound.

Step F: Preparation of 10,11-Dihydro-5-hydroxymethyl-5H-dibenzo[a,d]cyclohepten-5,10-imine A solution of 900 mg (2.7 mmole) of the N-BOC 5-carboxaldehyde of Step E in 15 mL of tetrahydrofuran was stirred under nitrogen in an ice bath as a solution containing 410 mg (10.8 mmole) of sodium borohydride and 1.0 mL of 1N sodium hydroxide in 10 ml ethanol was added dropwise. The ice bath was removed and the solution was allowed to stir at ambient temperature for 90 minutes by which time the reaction was complete by tlc (Silica GF, CHCl$_3$, CH$_3$OH, NH$_4$OH, 98:2:0.2). After removal of the solvents the crude N-BOC, 5-hydroxymethyl compound was extracted into dichloromethane and, upon washing and drying of the extracts, was isolated as a waxy solid: 800 mg; $^1$H NMR (300 MHz) (CHCl$_3$) δ: 1.46 (s, 9H, CH$_3$), 2.67 (d, 1H, J=17Hz, benzylic CH$_2$, endo), 3.60 (ABq, 1H, J=4.5Hz, DMAB=15.8Hz, benzylic CH$_2$, exo), 4.41 (d, 1H, J=12Hz, CH$_x$OH), 4.945 (ABq, 1H, J=10.3Hz, DMAB=7.9Hz, CH$_4$OH), 5.38 (d, 1H, J=5.4Hz, bridgehead methine), 5.77 (d, 1H, J=10Hz, OH), 6.92–7.50 (m, 8H, aryl).

The intermediate was de-protected by dissolving the 800 mg of solid in 20 mL of dichloromethane and, at 0° C., adding 5 mL of trifluoroacetic acid to the stirring solution. After one hour the reaction was complete by tlc (Silica GF, CHCl$_3$, CH$_3$OH, NH$_4$OH, 95:5:0.5) and the mixture was evaporated to a white solid: 400 mg, m.p. 208°–222° C. Recrystallization from acetonitrile affords pure 10,11-dihydro-5-hydroxymethyl-5H-dibenzo[a,d]cyclohepten-5,10-imine, m.p. 231°–232°.

EXAMPLE 11

5-Fluoromethyl-10,11-dihydro-5H-dibenzo[a,d]cyclohepten-5,10-imine

To a solution of 0.28 mL (3.5 mmol) of dry pyridine in 10.0 mL of dry dichloromethane, stirring in an ice-acetone bath, was added dropwise a solution containing 0.52 mL (3.1 mmol) of trifluoromethane sulfonic anhydride. The mixture was allowed to stir at 0° C. for 10 minutes before the dropwise addition of a solution of 0.71 g of the N-t-butylcarbamate derivative of 5-hydroxymethyl-10,11-dihydro-5H-dibenzo[a,d]cyclohepten-5,10-imine in 5 mL of methylene chloride. Stirring at 0° C. was continued for an additional 35 minutes after which time the solution was further diluted with 25 mL of methylene chloride. The solution was washed with ice-cold saturated sodium bicarbonate solution and dried over magnesium sulfate. The solvent was removed at 25° C. in vacuo, leaving a residue of approximately 0.70 g. This crude triflate was dissolved in 20 mL of freshly distilled tetrahydrofuran and the resulting solution was added to a stirred solution of tetrabutylammonium fluoride in tetrahydrofuran (11.0 mL, 1.0M) under a nitrogen atmosphere. The mixture was stirred at reflux for 2 hours, cooled and poured into a mixture of 50 mL of ether-20 mL of ethyl acetate. The combined organic phases were washed with 30 mL of a mixture of brine and saturated sodium bicarbonate, dried over magnesium sulfate, and, upon removal of the drying agent, evaporated to give 0.70 g of an oil which had two major components by thin layer chromatography: silica gel GF, CHCl$_3$:CH$_3$OH:NH$_4$OH (98:2:0.2). (Flash chromatography of the mixture in this solvent system afforded 180 mg of a by-product.)

Further elution provided 110 mg of an oil, 5-fluoromethyl-10,11-dihydro-5H-dibenzo[a,d]cyclohepten-5,10-imine. NMR (300 MHz) (CDCl$_3$) δ: 2.6–3.0 (broad s, 1H, NH), 2.75 (d, 1H, J=17Hz, C—11 endo methylene), 3.46 (dd, 1H, J=17, 5.6 Hz, C—11 exo methylene), 4.78 (d, 1H, C—10 methine), 5.23 (A), 5.39 (B) (dq, 2H, J$_{AB}$=9.8 Hz, J$_{AF}$=47.4 Hz, J$_{BF}$=47.1 Hz, Δν$_{AB}$=45.3 Hz, CH$_2$F), 6.9–7.4 (m, 8H, aromatic). An analytical sample of the latter compound was prepared by treating an acetone solution of the free base with ethanolic HCl until acidic, and stirring until crystallization was complete; m.p. 274°–282° C. (dec).

EXAMPLE 12

5-Fluoromethyl-10,11-dihydro-5H-dibenzo[a,d]cyclohepten-5,10-imine

A solution of 0.37 mL (3 mmole) of "DAST" (diethylaminosulfurtrifluoride) in 4 mL of 1,2-dichlorethane was stirred under nitrogen at −55° C. while a suspension of 5-hydroxymethyl-10,11-dihydro-5H-dibenzo[a,d]cyclohepten-5,10-imine (182 mg, 0.77 mmole) in 13 mL of the same solvent was added portionwise. When the addition was complete the cooling bath was replaced with an oil bath and the reaction mixture was heated to 75° C. The reaction was followed by thin layer chromatography (silica gel GF; $CHCl_3$: $CH_3OH$, 98:2) and as soon as the starting material spot had essentially disappeared and been replaced by faster, less polar material (within 24 hours) the reaction mixture was cooled in an ice bath and the reaction quenched by the addition of dilute aqueous sodium bicarbonate. The product mixture was extracted into dichloromethane, the combined organic phases washed sequentially with saturated sodium bicarbonate, water and brine, dried, and evaporated to afford 180 mg of an oil from which pure 5-fluoromethyl-10,11-dihydro-5H-dibenzo[a,d]cyclohepten-5,10-imine was obtained by flash chromatography ($CHCl_3$:$CH_3OH$, 98:2).

EXAMPLE 13

5-Fluoromethyl-10,11-dihydro-5H-dibenzo[a,d]cyclohepten-5,10-imine

Step A: Preparation of N-trifluoromethanesulfonyl-10,11-dihydro-5-hydroxymethyl-5H-dibenzo[a,d]cyclohepten-5,10-imine To a stirred solution of 868 mg (3.66 mmol) of 10,11-dihydro-5-hydroxymethyl-5H-dibenzo[a,d]cyclohepten-5,10-imine and 790 mg (3.84 mmol) of 2,6-di-t-butyl-4-methylpyridine (DBMP) in 40 mL of $CH_2Cl_2$ at 0° C. was added 646 μL (3.84 mmol) of trifluoromethanesulfonic anhydride (TFMSA) dropwise over a 3 minute period. After stirring at 0° C. for 1.0 hour, an additional 20 μL (0.01 mmol) of TFMSA and approximately 10 mg (0.05 mmol) of DBMP were added and stirring continued for 0.5 hour. The reaction mixture was poured into saturated $NaHCO_3$, and the aqueous layer extracted with 2×30 mL of $CHCl_3$. The combined organic layers were washed with water and brine, dried over $Na_2SO_4$, and the solvents removed at reduced pressure to give a yellow oil which was chromatographed on 200 g of $SiO_2$ using 1:4 ethyl acetate-hexanes. Workup of the column eluate afforded 920 mg (68%) of title compound as a colorless solid: m.p. 88°–90° C. $^{19}F$ NMR ($CD_3CN$) −75.00 ppm (s, $F_3C$—) $^1H$ NMR IR MS.

Step B: Preparation of Cyclic sulfamate

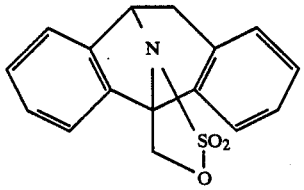

Treatment of 811 mg (2.2 mmol) of product from Step A with 20 mL of a 0.21M solution of tetra-n-butylammonium fluoride in $CH_3CN$ for 10 minutes at 20° C., followed by pouring the reaction mixture into 0.5M HCl, extraction with 100 mL of $CHCl_3$, drying over $Na_2SO_4$, and removing the solvents at reduced pressure afforded a yellow oil. This oil was chromatographed on 50 g of $SiO_2$ using 1:1 ethyl acetate-hexanes to give 356 mg (54%) of cyclic sulfamate as a colorless solid: m.p. 242°–244° C., $^1H$ NMR IR MS Anal. Calc'd for $C_{16}H_{13}NO_3S$ C, 64.20; H, 4.38; N, 4.68.

Found: C, 64.32; H, 4.35; N, 4.75.

Step C: Preparation of 5-fluoromethyl-10,11-dihydro-5H-dibenzo[a,d]cyclohepten-5,10-imine A. A stirred solution of 30 mg (0.1 mmol) of cyclic sulfamate in 1.2 mL of 0.21M tetra-n-butylammonium fluoride in $CH_3CN$ was heated at 70° C. for 25 minutes, followed by the addition of 20 mL of 3.0M HCl. After stirring for an additional 10 minutes at 70° C., the reaction mixture was poured into $CHCl_3$, and the aqueous layer washed with $CHCl_3$. The aqueous layer was basified with 5% NaOH and extracted with 2×25 mL of $CHCl_3$. The combined organic layers were washed with water and brine, dried over $Na_2SO_4$, and the solvents removed at reduced pressure to give 20 mg (84%) of the title compound as a colorless oil.

B. A solution of 764 mg (2.07 mmol) of product from Step A (cyclic sulfamate) in 40 mL of 0.21M tetra-n-butylammonium fluoride in $CH_3CN$ was heated at 70° for 20 minutes, followed by the addition of 40 mL of 3.0M HCl. After stirring for an additional 10 minutes at 70°, the reaction mixture was poured into $CHCl_3$ and worked up as in A above to give 394 mg of title compound as a colorless oil. An additional amount of it was obtained by treatment of the residue obtained from evaporation of the original $CHCl_3$ extract with 10% HCl for 10 minutes followed by the same workup to give a total of 526 mg which was chromatographed on $SiO_2$ using 98:2:0.2 $CHCl_3$—$CH_3OH$—$NH_4OH$ to give 351 mg (71%) of title compound as a colorless solid: m.p. 83°–85° C. $^{19}F$ NMR (−232.9) ppm (t, $J_{HF}=47$) $^1H$ NMR.

Anal. Calc'd for $C_{16}H_{14}FN$: C, 80.31; H, 5.90; N, 5.85.

Found: C, 80.56; H, 5.94; N, 5.98.

EXAMPLE 14

5-(2-Fluoroethyl)-10,11-dihydro-5H-dibenzo[a,d]cyclohepten-5,10-imine

Step A: Preparation of 10,11-Dihydro-5-(2-(t-butyldimethylsilyloxy)ethyl)-5H-dibenzo[a,d]cyclohepten-5,10-imine To a stirred solution of 200 mg (0.80 mmol) of 10,11-dihydro-5-(2-hydroxyethyl)-5H-dibenzo[a,d]cyclohepten-5,10-imine and 60 mg (0.88 mmol) of imidazole in 10 mL of $CH_2Cl_2$ was added a solution of 126 mg (0.84 mmol) of t-butyldimethylsilyl chloride in 2 mL of $CH_2Cl_2$ dropwise under $N_2$. After stirring for 2.0 hours at room temperature, the reaction mixture was poured into water and extracted with two portions of $CH_2Cl_2$. The combined organic layers were washed with water and brine, dried over $Na_2SO_4$, and the solvent removed at reduced pressure to give 317 mg (>100%) of title compound as an oil. $^1H$ NMR −0.01, 0.01 (2s, $(CH_3)_2Si$), 0.89 (s,$(CH_3)_3CSi$), 2.50–2.80 (m,$H_2C$—C(5), $H_{endo}$—C(11), H—N),3.45(dd,$J_1=17$, $J_2=5.5$ $H_{ex}$- o—C(11)), 3.85-3.99(m, H₂C—OSi), 4.70(d,J=5.5, H—C(10)), 6.90-7.35(m,8H-arom).

Step B: Preparation of 5-(2-t-Butyldimethylsilyloxy) ethyl)-10,11-dihydro-N-trifluoromethanesulfonyl-5H-dibenzo[a,d]cyclohepten-5,10-imine A stirred solution of 290 mg (0.80 mmol) of product from Step A and 180 mg (0.88 mmol) of 2,6-di-t-butyl-4-methylpyridine in 10 mL of CH₂Cl₂ was cooled to −10° C. and 147 μL (0.88 mmol) of trifluoromethanesulfonic anhydride was added dropwise. After stirring in the cold for 1.0 hours, the reaction mixture was poured into sat. NaHCO₃ and extracted with two portions of CH₂Cl₂. The combined organic layers were washed with 2% HCl, water, and dried over Na₂SO₄. Evaporation of the solvent at reduced pressure and chromatography on silica gel using 95:5 hexanes-ethyl acetate afforded 284 mg (72%) of the title compound as a colorless oil. ¹H NMR −0.01, 0.01 (2s,(CH₂)₂Si), 0.89 (s,(CH₃)₃CSi), 2.72(d,J=17, H$_{endo}$C(11)), 2.99-3.22 (m,H₂C—C(5)), 3.56-3.67(m,H—C—OSi), 3.84 (dd, J₁=17, J₂=5.5, H$_{exo}$—C(11)), 3.95-4.05 (m,H—C—OSi), 5.39(br d,J=5.5, H—C(10)), 6.95-7.38 (m,8H-arom).

Step C: Preparation of 5-(2-Fluoroethyl)-10,11-dihydro-5H-dibenzo[a,d]cyclohepten-5,10-imine A 154 mg (0.31 mmol) sample of product from Step B was heated at 65° C. for 20 minutes in 3.0 mL of a 0.21M solution of tetra-n-butylammonium fluoride in acetonitrile, followed by treatment with 4.0 mL of 3.0M HCl at 65° C. for 15 minutes. The reaction mixture was washed with two portions of CHCl₃, basified to pH 12 with 2.0M NaOH and extracted with two portions of CHCl₃. The combined extracts were washed with water, dried over Na₂SO₄, and evaporated at reduced pressure to provide an oil which was chromatographed on silica gel using 98:2:0.2 CHCl₃—CH₃OH—NH₄OH and crystallized from hexanes to give 38 mg (48%) of the title compound as colorless crystals. ¹H NMR, Anal. Calc'd for C₁₇H₁₆NF: C 80.60 H 6.37 N 5.53. Found: C 80.41 H 6.46 N 5.82

EXAMPLE 15

10,11-Dihydro-5-(2-hydroxyethyl)-10-hydroxy-5H-dibenzo[a,d]cyclohepten-5,10-imine To a stirred slurry of 1.23 g (32.4 mmol) of lithium aluminum hydride in 50 mL of ether at −5° C. was added a solution of 5.0 g (16.2 mmol) of 10,11-dihydro-5-carbethoxymethyl-10-hydroxy-5H-dibenzo[a,d]cyclohepten-5,10-imine in 60 mL of THF dropwise under N₂. After the addition, the cold bath was removed and stirring continued for 1 hour and 15 minutes. The mixture was recooled in an ice bath, and quenched by the careful addition of 1.23 mL of water, 1.23 mL of 15% NaOH, and 3.69 mL of water in that order. The resulting mixture was filtered, and the white precipitate washed with 50 mL of CHCl₃. The filtrate was washed with water and the aqueous layer was extracted with 150 mL of CHCl₃. The combined organic layers were washed with water, dried over Na₂SO₄ and the solvents removed to give a colorless foam which was crystallized from 160 mL of 1:3 ethyl acetate-hexanes to give 2.88 g (67%) of a colorless solid, m.p. 174°-176° C.

Employing the procedures substantially as described in the foregoing examples but substituting for the dibenzocycloheptenimine starting materials used therein in which R⁵ and R⁶ are hydrogen, derivatives thereof in which one or both of R⁵ and R⁶ are other than hydrogen, there are produced the corresponding fluoro and hydroxy derivatives.

EXAMPLE 16

Preparation of Intravenous Solutions

A solution containing 10 mg of 5-methyl-10,11-dihydro-11-exo-hydroxy-5H-dibenzo[a,d]cyclohepten-5,10-imine per mL of injectable solution is prepared in the following manner.

A mixture of 10 mg of active ingredient and 9 mg of sodium chloride is dissolved in sufficient water for injection to make 1 mL of solution. The pH is adjusted using hydrochloric acid for aqueous sodium hydroxide to about pH 7.0.

If it is desired that the intravenous solution be used for multi-dose purposes. 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg, respectively, of active ingredient per mL of solution are similarly prepared substituting the indicated amount for the above-illustrated 10 mg quantity. Bulk injectable solutions of convenient volume for subsequent delivery in unit dosage form are readily prepared following the above procedure.

Following the above procedure, other representative injectable solutions of the present invention are prepared when 5-methyl-10,11-dihydro-11-exo-hydroxy-5H-dibenzo[a,d]cyclohepten-5,10-imine is replaced by an equivalent amount of any of the other novel compounds of the present invention.

EXAMPLE 17

Tablet Preparation

Tablets containing 1.0, 2.0, 25.0, 26.0, 50.0 and 100.0 mg, respectively, of 5-methyl-10,11-dihydro-11-exo-hydroxy-5H-dibenzo[a,d]cyclohepten-5,10-imine are prepared as illustrated below.

| TABLE FOR DOSES CONTAINING FROM 1-25 MG OF THE ACTIVE COMPOUND | | | |
|---|---|---|---|
| | Amount - mg | | |
| 5-Methyl-10,11-dihydro-11-exo-hydroxy-5H—dibenzo[a,d]cyclohepten-5,10-mine | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-200 MG OF THE ACTIVE COMPOUND | | | |
|---|---|---|---|
| | Amount - mg | | |
| 5-Methyl-10,11-dihydro-11-exo-hydroxy-5H—dibenzo[a,d]cyclohepten-5,10-imine hydrogen maleate | 26.0 | 50.0 | 100.0 |
| Microcrystalline cellulose | 25.0 | 100.0 | 100.0 |

-continued

TABLE FOR DOSES CONTAINING FROM
26–200 MG OF THE ACTIVE COMPOUND

|  | Amount - mg | | |
| --- | --- | --- | --- |
| Modified food corn starch | 2.21 | 4.25 | 8.5 |
| Magnesium stearate | .39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet. Other tablets are prepared using the same procedures and the equivalent amounts of excipients along with equivalent amounts of any of the novel compounds of the present invention.

What is claimed is:

1. A compound of structural formula:

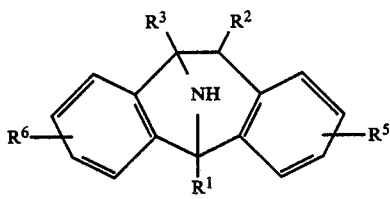

or a pharmaceutically acceptable salt thereof, wherein
$R^2$ is
 (1) hydrogen,
 (2) hydroxy, or
 (3) fluoro;
$R^3$ is
 (1) hydrogen, or
 (2) fluoro, and
$R^1$ is
 (1) —CH$_2$F,
 (2) —(CH$_2$)$_2$F
 (3) —CH$_2$OH,
 (4) —CH$_3$,
 (5) —CH(OH)COOR$^4$, wherein R$^4$ is C$_{1-3}$ alkyl,
 (6) —CH(OH)CH$_2$OH,
 (7) —CH$_2$CH$_2$OH, or
 (8) —CH$_2$CH$_3$;
$R^5$ and $R^6$ are independently
 (1) hydrogen,
 (2) halogen,
 (3) C$_{1-5}$ alkoxy,
 (4) trifluoromethylthio,
 (5) cyano,
 (6) carboxy, or
 (7) hydroxy,
with the proviso that if both $R^2$ and $R^3$ are hydrogen, $R^1$ is not —CH$_3$, —CH$_2$CH$_3$ or —CH$_2$CH$_2$OH.

2. The compound claim 1 of structural formula:

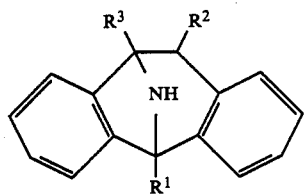

or a pharmaceutically acceptable salt thereof, wherein
$R^2$ is
 (1) hydrogen,
 (2) hydroxy, or
 (3) fluoro;
$R^3$ is
 (1) hydrogen, or
 (2) fluoro, and
$R^1$ is
 (1) —CH$_2$F,
 (2) —(CH$_2$)$_2$F
 (3) —CH$_2$OH,
 (4) —CH$_3$,
 (5) —CH(OH)COOR$^4$, wherein R$^4$ is C$_{1-3}$ alkyl,
 (6) —CH(OH)CH$_2$OH,
 (7) —CH$_2$CH$_2$OH, or
 (8) —CH$_2$CH$_3$;
with the proviso that if both $R^2$ and $R^3$ are hydrogen, then $R^1$ is not —CH$_3$, CH$_2$CH$_3$ or —CH$_2$CH$_2$OH.

3. The compound of claim 2 selected from:
5-methyl-10,11-dihydro-11-endo-hydroxy-5H-dibenzo[a,d]cyclohepten-5,10-imine;
5-methyl-10,11-dihydro-11-exo-hydroxy-5H-dibenzo[a,d]cyclohepten-5,10-imine;
5-methyl-10,11-dihydro-10-hydroxy-5H-dibenzo[a,d]cyclohepten-5,10-imine;
5-Hydroxymethyl-10,11-dihydro-5H-dibenzo[a,d]cyclohepten-5,10-imine;
5-methyl-10,11-dihydro-11-fluoro-5H-dibenzo[a,d]cyclohepten-5,10-imine;
5-methyl-10,11-dihydro-10-fluoro-5H-dibenzo[a,d]cyclohepten-5,10-imine;
5-fluoromethyl-10,11-dihydro-5H-dibenzo[a,d]cyclohepten-5,10-imine;
5R-(1-Ethoxycarbonyl-1-hydroxy-12R)methyl-10,11-dihydro-5H-dibenzo[a,d]cyclohepten-5,10-imine; and
5-(1,2-Dihydroxyethyl)-10,11-dihydro-5H-dibenzo[a,d]cyclohepten-5,10-imine;
5-(2-Hydroxyethyl)-10-hydroxy-10,11-dihydro-5H-dibenzo[a,d]-cyclohepten-5,10-imine;
5-(2-Fluoroethyl)-10,11-dihydro-5H-dibenzo[a,d]-cyclohepten-5,10-imine
or a pharmaceutically acceptable salt thereof.

4. 5-Methyl-10,11-dihydro-11-endo-hydroxy-5H-dibenzo[a,d]-cyclohepten-5,10-imine.

5. A pharmaceutical composition for the treatment of convulsions caused by N-methyl-D-aspartate comprising a pharmaceutical carrier and an effective anticonvulsant amount of the compound of claim 1, or a pharmaceutically acceptable salt thereof.

6. A pharmaceutical composition for the treatment of convulsions caused by N-methyl-D-aspartate comprising a pharmaceutical carrier and an effective anticonvulsant amount of the compound of claim 2, or a pharmaceutically acceptable salt thereof.

7. The pharmaceutical composition of claim 6, wherein the compound is selected from:

5-methyl-10,11-dihydro-11-endo-hydroxy-5H-dibenzo[a,d]cyclohepten-5,10-imine;
5-methyl-10,11-dihydro-11-exo-hydroxy-5H-dibenzo[a,d]cyclohepten-5,10-imine;
5-methyl-10,11-dihydro-10-hydroxy-5H-dibenzo[a,d]cyclohepten-5,10-imine;
5-Hydroxymethyl-10,11-dihydro-5H-dibenzo[a,d]cyclohepten-5,10-imine;
5-methyl-10,11-dihydro-11-fluoro-5H-dibenzo[a,d]cyclohepten-5,10-imine;
5-methyl-10,11-dihydro-10-fluoro-5H-dibenzo[a,d]cyclohepten-5,10-imine;
5-fluoromethyl-10,11-dihydro-5H-dibenzo[a,d]cyclohepten-5,10-imine;
5R-(1-Ethoxycarbonyl-1-hydroxy-12R)methyl-10,11-dihydro-5H-dibenzo-[a,d]cyclohepten-5,10-imine; and
5-(1,2-Dihydroxyethyl)-10,11-dihydro-5H-dibenzo[a,d]cyclohepten-5,10-imine;
5-(2-Fluoroethyl)-10,11-dihydro-5H-dibenzo[a,d]-cyclohepten-5,10-imine
5-(2-Hydroxyethyl)-10-hydroxy-10,11-dihydro-5H-dibenzo[a,d]-cyclohepten-5,10-imine;
or a pharmaceutically acceptable salt thereof.

8. A method of treating convulsions caused by N-methyl-D-aspartate which comprises the administration to a patient in need of such treatment of an effective anticonvulsant amount of the compound of claim 1, or a pharmaceutically acceptable salt thereof.

9. A method of treating convulsions which comprises the administration to a patient in need of such treatment of an effective anticonvulsant amount of the compound of claim 2, or a pharmaceutically acceptable salt thereof.

10. The method of claim 9 wherein the compound is selected from:
5-methyl-10,11-dihydro-11-endo-hydroxy-5H-dibenzo[a,d]cyclohepten-5,10-imine;
5-methyl-10,11-dihydro-11-exo-hydroxy-5H-dibenzo[a,d]cyclohepten-5,10-imine;
5-methyl-10,11-dihydro-10-hydroxy-5H-dibenzo[a,d]cyclohepten-5,10-imine;
5-Hydroxymethyl-10,11-dihydro-5H-dibenzo[a,d]cyclohepten-5,10-imine;
5-methyl-10,11-dihydro-11-fluoro-5H-dibenzo[a,d]cyclohepten-5,10-imine;
5-methyl-10,11-dihydro-10-fluoro-5H-dibenzo[a,d]cyclohepten-5,10-imine;
5-fluoromethyl-10,11-dihydro-5H-dibenzo[a,d]cyclohepten-5,10-imine;
5R-(1-Ethoxycarbonyl-1-hydroxy-12R)methyl-10,11-dihydro-5H-dibenzo-[a,d]cyclohepten-5,10-imine; and
5-(1,2-Dihydroxyethyl)-10,11-dihydro-5H-dibenzo[a,d]cyclohepten-5,10-imine;
5-(2-Fluoroethyl)-10,11-dihydro-5H-dibenzo[a,d]cyclohepten-5,10-imine
5-(2-Hydroxyethyl)-10-hydroxy-10,11-dihydro-5H-dibenzo[a,d]-cyclohepten-5,10-imine;
or a pharmaceutically acceptable salt thereof.

* * * * *